US009192284B2

(12) United States Patent
Hirsch et al.

(10) Patent No.: US 9,192,284 B2
(45) Date of Patent: Nov. 24, 2015

(54) ENDOSCOPIC ACCESSORY FOR ENDOSCOPIC DEVICE

(75) Inventors: Yoav Hirsch, Modiin (IL); Izhak Fabian, Kfar Truman (IL)

(73) Assignee: EasyNotes Ltd., Kfar Truman (IL)

( * ) Notice: Subject to any disclaimer, the term of this patent is extended or adjusted under 35 U.S.C. 154(b) by 198 days.

(21) Appl. No.: 13/438,174

(22) Filed: Apr. 3, 2012

(65) Prior Publication Data
US 2013/0261390 A1    Oct. 3, 2013

(51) Int. Cl.
A61B 1/04 (2006.01)
A61B 1/00 (2006.01)
A61B 1/015 (2006.01)
A61M 1/00 (2006.01)

(52) U.S. Cl.
CPC ............. *A61B 1/00135* (2013.01); *A61B 1/015* (2013.01); *A61M 1/0062* (2013.01)

(58) Field of Classification Search
USPC ......... 600/104, 106, 114–116, 121–125, 127, 600/129, 156–159
See application file for complete search history.

(56) References Cited

U.S. PATENT DOCUMENTS

| 5,353,783 | A  | * | 10/1994 | Nakao et al. | 600/106 |
| 6,293,909 | B1 | * | 9/2001  | Chu et al.   | 600/121 |
| 2005/0256373 | A1 | * | 11/2005 | Bar-Or et al. | 600/114 |
| 2007/0142709 | A1 | * | 6/2007  | Martone et al. | 600/121 |
| 2009/0259172 | A1 | * | 10/2009 | Yamaoka et al. | 604/26 |
| 2009/0287049 | A1 | * | 11/2009 | Jones et al. | 600/115 |
| 2010/0063358 | A1 | * | 3/2010  | Kessler | 600/121 |
| 2010/0256447 | A1 | * | 10/2010 | Dubi et al. | 600/115 |

* cited by examiner

*Primary Examiner* — Ryan Henderson
(74) *Attorney, Agent, or Firm* — Dekel Patent Ltd.; David Klein

(57) ABSTRACT

An endoscopic system including an accessory that fits over an endoscopic device, the accessory including at least one collapsible tube which has a collapsed state and an expanded state, wherein in the collapsed state, the accessory increases an outer perimeter of the endoscopic device by not more than 10%, and in the expanded state, the at least one collapsible tube has fluid that flows therethrough and the accessory increases the outer perimeter of the endoscopic device by at least 10%.

11 Claims, 5 Drawing Sheets

ENDOSCOPIC ACCESSORY FOR ENDOSCOPIC DEVICE

FIELD OF THE INVENTION

The present invention relates generally to an endoscopic accessory for an endoscopic device, such as a collapsible tube or sleeve with irrigation and suction capability for navigating and imaging body lumens, such as the gastrointestinal (GI) tract, and an applicator for assembling the accessory on the endoscopic device.

BACKGROUND OF THE INVENTION

PCT Patent Application WO 2010/138521 describes an improved endoscopic device for performing endoscopy in a body lumen, such as the GI tract. The device includes an irrigation lumen (irrigation includes, inter alia, cleaning and/or washing) that provides a jet of cleaning fluid that cleans the body lumen during imaging thereof. Debris is sucked through a suction tube for discarding. Cleaning may be performed during imaging, during insertion of the endoscope, during withdrawing, and any combinations thereof. The device enhances performance of an endoscope for use with a body lumen that has not been sufficiently cleaned for viewing with the endoscope, which is particularly useful for colonoscopy.

SUMMARY OF THE INVENTION

The present invention seeks to provide an endoscopic accessory for an endoscopic device, such as a collapsible tube or sleeve with irrigation and suction capability for navigating and imaging body lumens, such as the GI tract, as is described more in detail hereinbelow.

There is thus provided in accordance with an embodiment of the present invention

BRIEF DESCRIPTION OF THE DRAWINGS

The present invention will be understood and appreciated more fully from the following detailed description taken in conjunction with the drawings in which:

FIGS. 5-8 are simplified pictorial illustrations of using the applicator to mount an accessory (e.g., collapsible tubes) on an endoscope, in accordance with an embodiment of the present invention, wherein:

FIG. 5 illustrates the endoscope inserted through the applicator, with the distal tip of the applicator mounted on the distal end of the endoscope;

FIG. 6 illustrates pulling back (proximally) the applicator and rear connector, thereby spreading the collapsible tubes, wherein the rear connector is then pushed forwards (distally) to move off the applicator;

FIG. 7 illustrates separating the left and right halves of the applicator and discarding them;

FIG. 8 illustrates moving the rear connector proximally to the endoscope handle, thereby completing the deployment (spreading) of the collapsible tubes, wherein the rear connector is attached to the endoscope handle, such as by means of a Velcro strap;

DETAILED DESCRIPTION OF EMBODIMENTS

Figure 1:
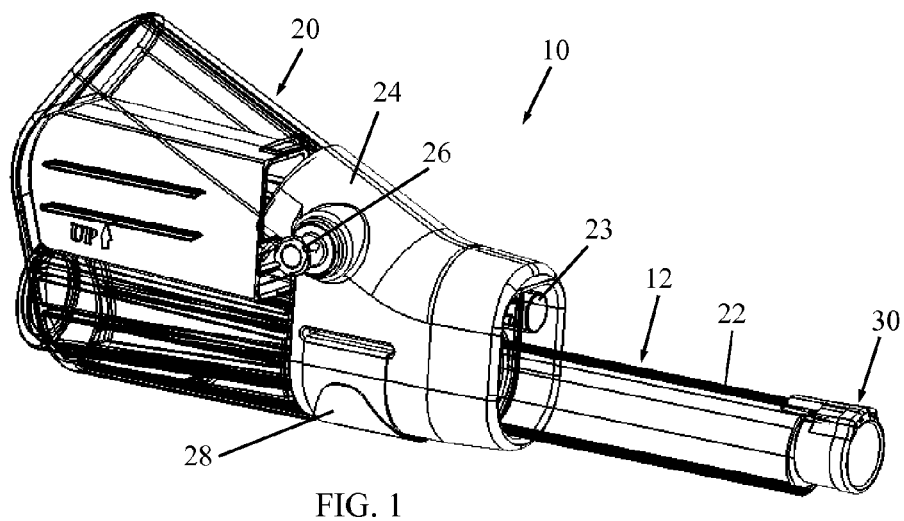
FIG. 1 is a simplified pictorial illustration of an applicator for assembling an endoscopic accessory on to an endoscopic device, the accessory including an irrigation and suction head, constructed and operative in accordance with an embodiment of the present invention.

Reference is now made to FIGS. 1-4, which illustrate an applicator 10 for assembling an endoscopic accessory 12 (such as, but not limited to, one or more collapsible tubes) on to an endoscopic device (shown later), in accordance with an embodiment of the present invention. Optionally, accessory 12 can be supplied with the endoscopic device, and already assembled thereon, by the endoscope manufacturer.

In the non-limiting illustrated embodiment, applicator 10 includes a left half 14 and a right half 16, which may be made of an injection-moldable plastic, for example. Each half includes a housing half 17 from which a tubing-half 18 extends distally. The two housing halves cover a collapsible tube cartridge 20, for housing therein collapsible tubes 22, which may be typically made of a flexible, foldable plastic. (Folds of the collapsible tubes 22 are seen partially in FIG. 1, but mostly omitted for clarity.) The two halves 14 and 16 may snap-fit together or may be otherwise joined for easy removal.

As will be explained later, one of the collapsible tubes 22 will be used for irrigation, wherein the irrigation fluid (e.g., water, saline, etc.) expands the lumen of the collapsible tube as it flows through the tube. Another of the collapsible tubes 22 will be used for suction, wherein a non-collapsible suction tube will be inserted in the collapsible suction tube. The collapsible suction tube is filled out by the non-collapsible suction tube being inserted therein and passed therethrough. The collapsible tubes are in a collapsed state for insertion in the body lumen, which makes passage through the body lumen much easier than the prior art. The collapsible tubes are filled out (either with irrigation fluid or the non-collapsible suction tube) only after they have been inserted in the body lumen. Thus, in contrast with the prior art, which tries to force non-collapsible tubes in the body lumen, in the present invention, the tubes are inserted in a collapsed state and only afterwards expanded.

A rear connector 24 is mounted on tubing-halves 18. A proximal face of rear connector 24 abuts against a distal face of collapsible tube cartridge 20. Rear connector 24 includes a (e.g., check) valve 26 for fluid connection to irrigation tubing (not shown). Rear connector 24 includes an attachment device 28, such as but not limited to, a Velcro strap, band, retaining ring, clamp, or by any other suitable means of joining or attaching rear connector 24 to the endoscope (not shown here). The proximal end of collapsible tube 22 is connected to a port 23 on rear connector 24. Port 23 is shown in the illustrated embodiment as being distal to the collapsible tube cartridge 20, but it is understood that port 23 may be positioned in other places. The collapsible tube 22 will pay out neatly from collapsible tube cartridge 20, and when stretched out, will be completely distal to port 23.

Figure 2A:
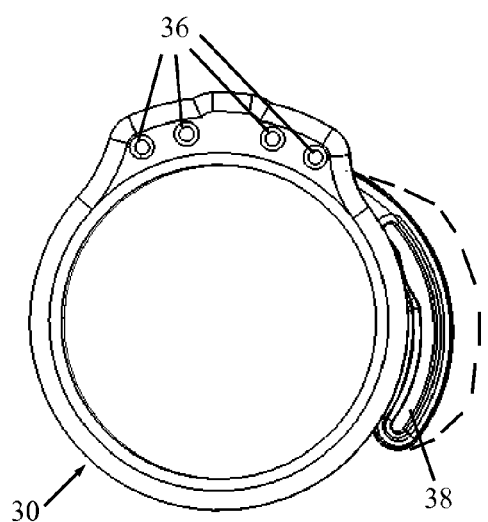
FIGS. 2A and 2B are simplified front-view and perspective illustrations of the irrigation and suction head, in accordance with an embodiment of the present invention.
Figure 2B:
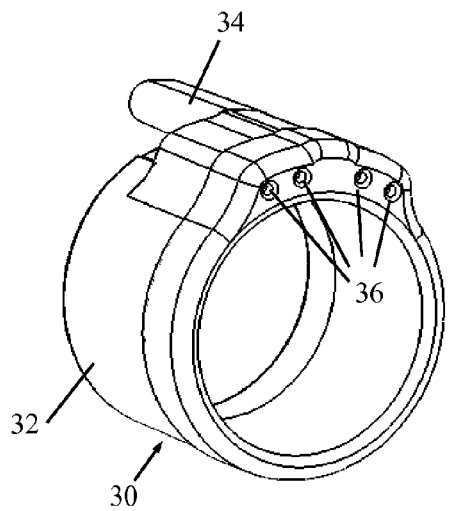
Figure 3:
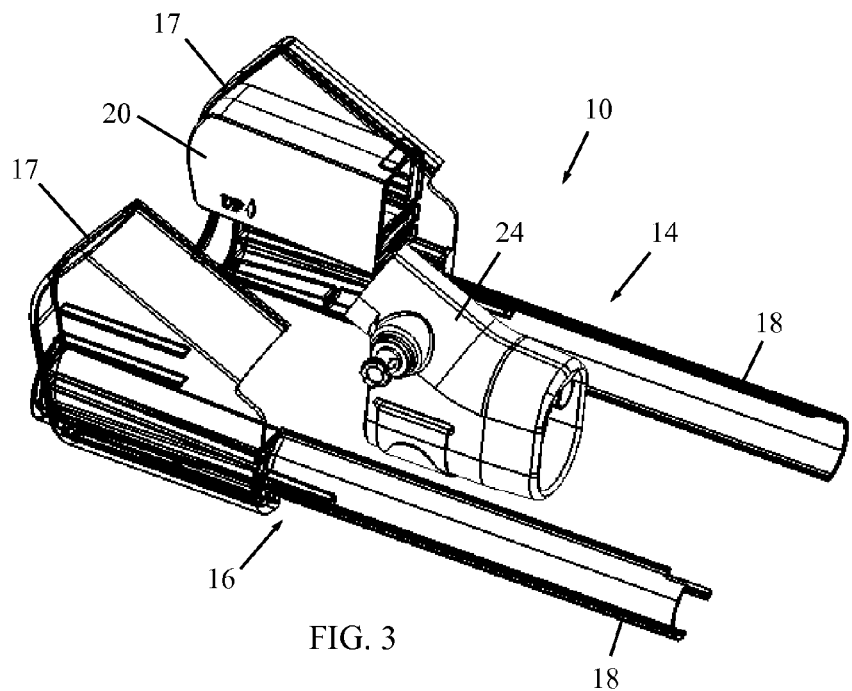
FIG. 3 is a simplified pictorial illustration of the applicator, showing a collapsible tube cartridge, left and right halves of the applicator and rear connector, in accordance with an embodiment of the present invention.
Figure 4:
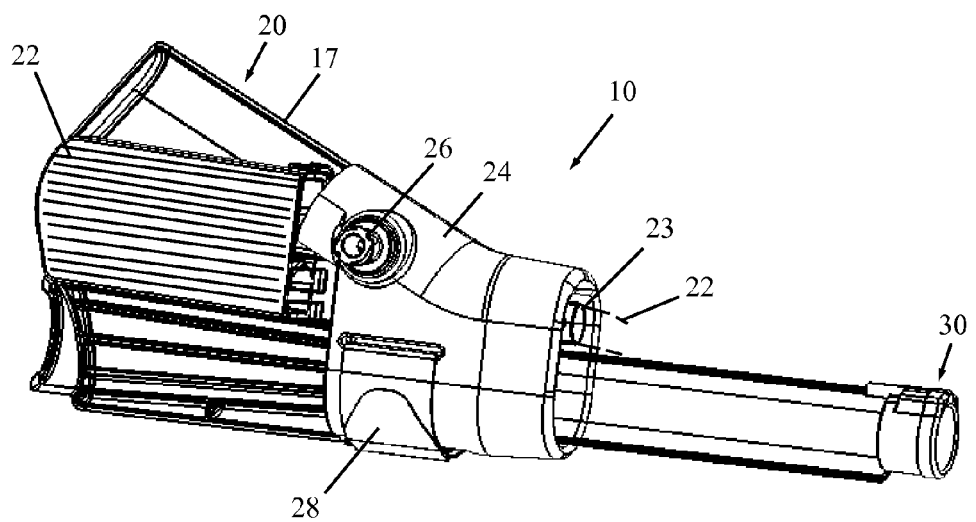
FIG. 4 is a simplified pictorial illustration of the left half of the applicator, showing the position of the collapsible tubes folded in the cartridge, attached at a proximal end to the rear connector and at a distal end to the irrigation and suction head.

The distal end of one collapsible tube 22 is connected to an irrigation and suction head 30, which is now described with reference to FIGS. 2A and 2B. Irrigation and suction head 30 includes a ring 32, having a proximally-directed irrigation port 34 which is in fluid communication with one or more distally-directed irrigation outlet ports 36 (e.g., nozzles). A suction tube port 38 is attached to an outer perimeter of ring 32. As seen in FIG. 2A, suction tube port 38 extends radially outwards from ring 32, and is initially arc-shaped ("banana" shaped), but can expand radially outwards to a more rounded shape (shown in broken lines in FIG. 2A) when a suction tube (shown later) is inserted therein.

Reference is now made to FIGS. 5-8, which illustrate using the applicator 10 to mount accessory 12 (comprising collapsible tubes 22) on an endoscope 40, in accordance with an embodiment of the present invention.

Figure 5:
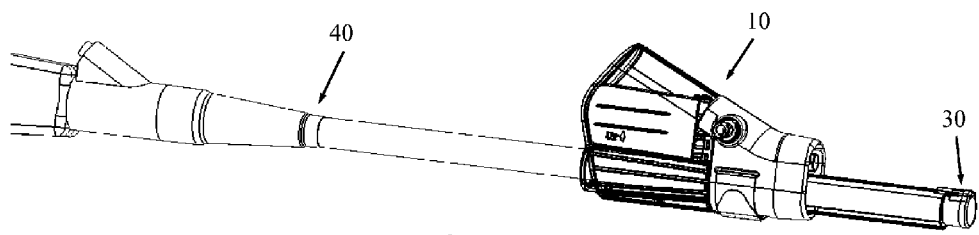

In FIG. 5, endoscope 40 is inserted through applicator 10. Irrigation and suction head 30 at the distal tip of applicator 10 is placed on the distal end of endoscope 40.

Figure 6:
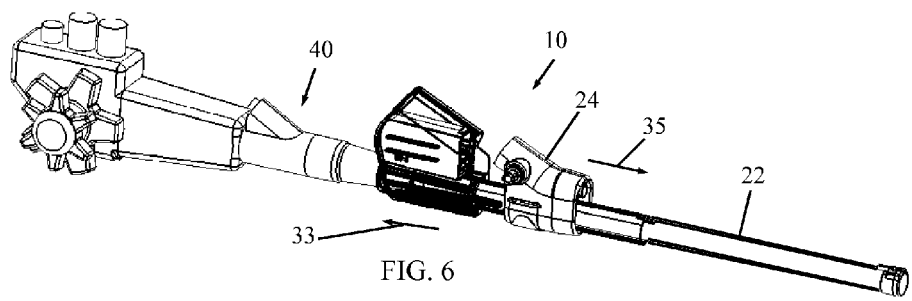

In FIG. 6, applicator 10, along with rear connector 24, is pulled back proximally in the direction of arrow 33. This causes collapsible tube 22 to spread out lengthwise. The rear connector 24 is then pushed forwards (distally, in the direction of arrow 35) to move off applicator 10.

Figure 7:
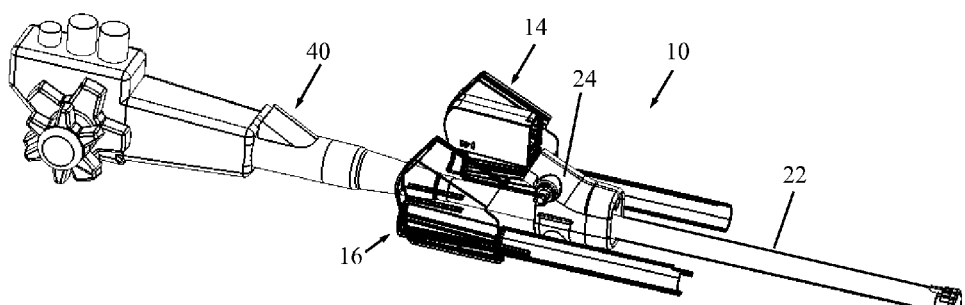

In FIG. 7, the left and right halves 14 and 16 of applicator 10 are separated and discarded.

Figure 8:
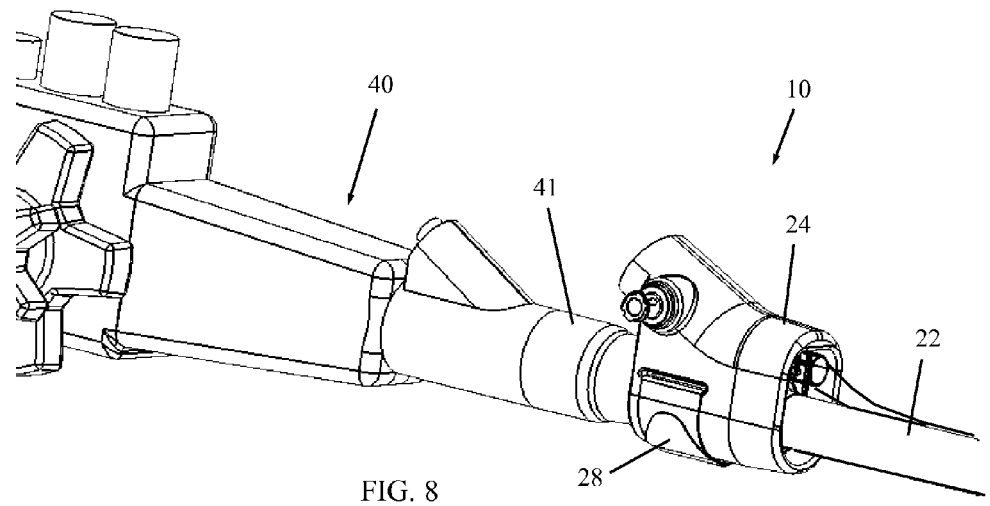

In FIG. 8, rear connector 24 is moved proximally to handle 41 of endoscope 40. This completes the deployment (spreading) of collapsible tube 22. Rear connector 24 is attached to endoscope handle 41 by means of attachment device 28.

Figure 9:
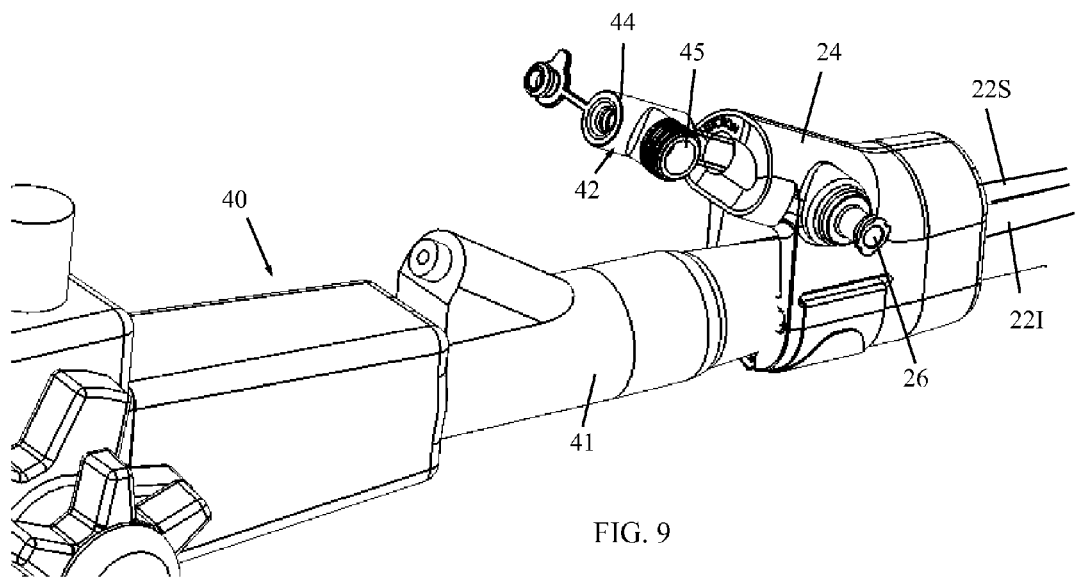
FIG. 9 is a simplified pictorial illustration of a non-collapsible suction tube inserted through a suction tube port of the rear connector (the suction tube will then pass through the collapsible suction tube), wherein fluid connection to collapsible irrigation tubing is through a check valve mounted in the rear connector and fluid connection to suction tubing is through a suction connector mounted in the rear connector.

Reference is now made to FIG. 9. A non-collapsible suction tube 42 is inserted completely through rear connector 24. Suction tube 42 passes through collapsible suction tube 22S. The collapsible suction tube 22S is filled out by the non-collapsible suction tube 42 inserted therein and passed therethrough. Tools (not shown) may also be inserted through an access port 44. Suction connection (from a vacuum source, not shown) to suction tube 42 is through a suction connector 45 mounted on tube 42. Fluid connection to collapsible irrigation tube 22I is through check valve 26. The irrigation fluid (e.g., water, saline, etc.) expands the lumen of the collapsible irrigation tube 22I as it flows through tube 22I. When the collapsible tubes 22I and 22S are in the collapsed state, accessory 12 increases the outer perimeter of endoscope 40 by not more than 10%. When the collapsible tubes 22I and 22S are in the expanded state, accessory 12 increases the outer perimeter of endoscope 40 by more than 10%.

Figure 10:
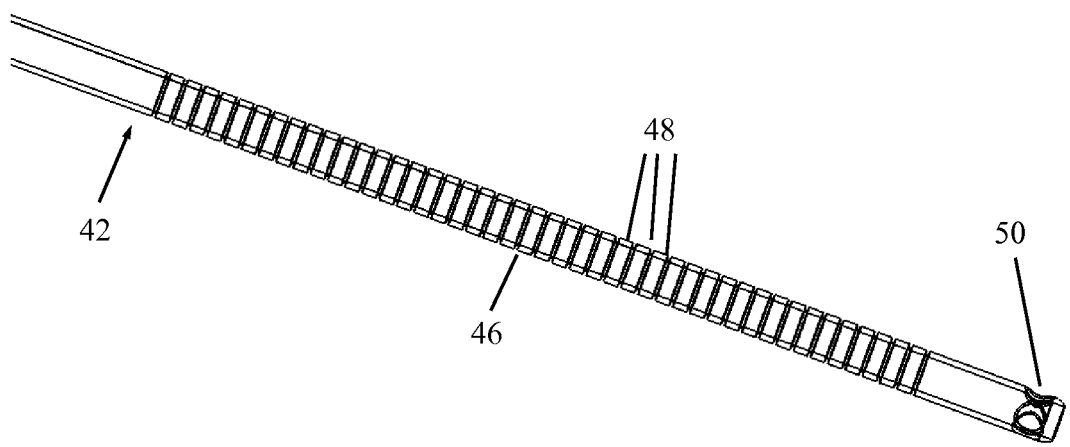
FIG. 10 is a simplified pictorial illustration of the non-collapsible suction tube, having an articulating portion, in accordance with an embodiment of the present invention.

Reference is now made to FIG. 10, which illustrates suction tube 42, in accordance with an embodiment of the present invention. Suction tube 42 may be made of polytetrafluoroethylene (PTFE). A distal portion (such as but not limited to 10-15 cm) of suction tube 42 is an articulation portion 46, which may include peripheral grooves 48 (axially spaced about 2 mm, without limitation). The distal tip may be formed with one or more peripheral venting holes 50.

A variety of sequence of operations can be used in employing the endoscopic system of the invention, such as but not limited to, different sequences of alternating between spraying jets of fluid to clean away debris in the body lumen, sucking the debris away, cleaning debris away from the drain outlet, including different time durations of each part of the sequence, frequency and amplitude of the jet sprays and suction, all of which may be automatically or manually controlled by the operator.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An endoscopic system comprising:
   an accessory that fits over an endoscopic device, said accessory comprising at least one collapsible tube which has a collapsed state and an expanded state;
   an applicator for assembling said accessory on said endoscopic device, wherein proximal and distal portions of said at least one collapsible tube are stored in a collapsible tube cartridge when said at least one collapsible tube is in the collapsed state, and wherein said applicator comprises a left half and a right half that cover said collapsible tube cartridge; and
   an irrigation and suction head formed with a through hole and comprising at least one of an irrigation port and a suction port, wherein a distal end of the endoscopic device is mounted within the through hole, a proximal end of said at least one collapsible tube is coupled to a port of said rear connector and a distal end of said at least one collapsible tube is coupled to said at least one of the irrigation port or the suction port; and wherein said applicator is detachably coupled to said rear connector, wherein said rear connector is attached to said endoscopic device by an attachment device upon detachment of said applicator from said rear connector, and wherein said irrigation and suction head comprises a ring, having a proximally-directed irrigation port which is in fluid communication with one or more distally-directed irrigation outlet ports, and a suction tube port attached to an outer perimeter of said ring.

2. The endoscopic system according to claim 1, wherein said at least one collapsible tube comprises a collapsible irrigation tube and a collapsible suction tube.

3. The endoscopic system according to claim 1, wherein said suction tube port is expandable radially outwards.

4. The endoscopic system according to claim 1, wherein said rear connector comprises a valve for fluid connection to irrigation tubing.

5. The endoscopic system according to claim 1, wherein in the expanded state, said at least one collapsible tube comprises a collapsible irrigation tube that has irrigation fluid that flows therethrough.

6. The endoscopic system according to claim 1, wherein in the expanded state, said at least one collapsible tube comprises a collapsible suction tube that has a non-collapsible suction tube inserted therein.

7. The endoscopic system according to claim 6, wherein a distal portion of said collapsible suction tube comprises an articulation portion.

8. The endoscopic system according to claim 6, wherein said collapsible suction tube comprises peripheral grooves.

9. The endoscopic system according to claim 6, wherein said collapsible suction tube comprises one or more peripheral venting holes.

10. The endoscopic system according to claim 1, wherein each of said left and right halves of said applicator comprises a housing half from which a tubing-half extends distally.

11. The endoscopic system according to claim 10, wherein said rear connector is mounted on said tubing-halves and a proximal face of said rear connector abuts against a distal face of said collapsible tube cartridge.

* * * * *